(12) United States Patent
Sackmann et al.

(10) Patent No.: US 6,590,040 B2
(45) Date of Patent: Jul. 8, 2003

(54) PROCESS FOR THE CONTINUOUS PRODUCTION OF SUPERABSORBENT POLYMERS FROM PAN EMULSIONS

(75) Inventors: Günter Sackmann, Leverkusen (DE); Rolf-Volker Meyer, Much (DE); Sergei Schapowalow, Saratov (RU); Telman Bayburdov, Saratov (RU); Jgor Nakonetschny, Saratov (RU)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/878,553

(22) Filed: Jun. 11, 2001

(65) Prior Publication Data

US 2002/0042478 A1 Apr. 11, 2002

(30) Foreign Application Priority Data

Jun. 16, 2000 (DE) .......................................... 100 29 876

(51) Int. Cl.⁷ .......................... C08F 20/44; C08F 120/44
(52) U.S. Cl. ................... 525/329.1; 523/324; 523/348; 523/353; 524/565; 524/566; 525/369
(58) Field of Search ................................ 524/565, 566; 523/348, 353, 324; 525/329.1, 369

(56) References Cited

U.S. PATENT DOCUMENTS

| 4,337,328 A | 6/1982 | Holst et al. .................. 525/336 |
| 4,931,510 A | 6/1990 | Sackmann et al. ........... 525/302 |
| 5,013,794 A | 5/1991 | Sackmann et al. ........... 525/203 |
| 5,350,799 A | * 9/1994 | Woodrum et al. .......... 525/54.3 |
| 5,356,985 A | 10/1994 | Sackmann et al. ........... 524/460 |
| 5,496,890 A | 3/1996 | Sackmann et al. ....... 525/329.1 |
| 5,567,779 A | 10/1996 | Sackmann et al. ....... 525/329.1 |
| 5,635,569 A | 6/1997 | Sackmann et al. ........... 525/367 |
| 5,728,774 A | 3/1998 | Sackmann et al. .......... 525/196 |

FOREIGN PATENT DOCUMENTS

SU 806690 * 2/1981

* cited by examiner

*Primary Examiner*—Judy M. Reddick
(74) *Attorney, Agent, or Firm*—Joseph C. Gil; Aron Preis

(57) ABSTRACT

A process for producing a superabsorbent polymer is described. The process that entails a continuous hydrolysis of an aqueous emulsion of crosslinked or uncrosslinked polyacrylonitrile in the form of fine particles is carried out in a cascade of stirred tanks. The reaction with alkali-hydroxide solution an aqueous-alcoholic medium at 60 to 100° C. yields polymers that are suitable for the preparation of hygiene products, water-storing materials in agriculture, and sheathing of electrical cables.

11 Claims, 1 Drawing Sheet

PROCESS FOR THE CONTINUOUS PRODUCTION OF SUPERABSORBENT POLYMERS FROM PAN EMULSIONS

FIELD OF THE INVENTION

The present invention relates to a process for the continuous production of superabsorbent polymers based on fine-particle, uncrosslinked and crosslinked aqueous polyacrylonitrile emulsions.

BACKGROUND OF THE INVENTION

Superabsorbent polymers are known and are principally employed in the production of diapers and incontinence articles. These polymers are also used as water-storing materials in agriculture and also for the sheathing of electrical cables. As a rule, the commercially available superabsorbent polymers are wide-mesh-crosslinked, water-insoluble polymers based on alkali salts of polyacrylic acid or based on copolymers of acrylic acid and acrylamide which are obtained by radically initiated co-polymerisation of acrylic acid and polyfunctional monomers such as, for example, divinylbenzene, ethylene glycol dimethacrylate, ethylene glycol diallyl ether, butane-diol acrylate, hexanediol methacrylate, polyglycol diacrylate, trimethylolpropane diacrylate, allyl acrylate, diallylacrylamide, triallylamine, diallyl ether, methylene-bisacrylamide and N-methylolacrylamide. By reason of their molecular structure, such polymers are capable of absorbing large amounts of liquids, accompanied by swelling and formation of hydrogels, and of retaining said liquids even under pressure.

Superabsorbent polymers with extremely high swelling power and high gel strengths are described in patent applications EP-A-670 335 and EP-A-697 416. These products are obtained by alkaline hydrolysis of polyacrylonitrile (PAN) emulsions at 50–100° C. and at reaction-times of 1 to 2 hours. With this process, products having superabsorbent properties are isolated after hydrolysis in the form of fine-particle powders by precipitating with solvents such as aliphatic monoalcohols, for example. After filtration and drying, the superabsorbent polymers are ground to the desired particle size.

The fine-particle, aqueous, high-molecular, uncrosslinked or crosslinked polyacrylonitrile emulsions that are required for production of the superabsorbent polymers are obtained by the homopolymerisation and/or copolymerisation of acrylonitrile in the presence of special anionic polymeric emulsifiers (see patent applications EP-A-331066 and also EP-A-590 460). The molecular weights of the uncrosslinked polyacrylonitrile emulsions that are prepared by this process lie within the range from $5–10^5$ to $1–10^7$ g/mol. The particle sizes of the uncrosslinked or crosslinked aqueous PAN emulsions lie within the range between 100 and 300 nm (determined by means of laser correlation spectroscopy).

In the course of the hydrolysis of such PAN emulsions with aqueous solutions of alkali hydroxides the partially hydrolysed homopolymers and/or copolymers of acrylonitrile are formed, in which 30 to 80 mol. % of the nitrile groups have been transformed into carboxylate groups and 20 to 70 mol. % of the nitrile groups have been transformed into carboxamide groups and 0 to 20 mol. % of the nitrile groups remain unchanged.

By reason of the transition, which occurs with incipient hydrolysis, from the low-viscosity PAN emulsions to the high-viscosity, water-swollen gelatinous state, a continuous implementation of the processes that have been described is not practicable in conventional stirring apparatus. Special apparatus is required for the continuous processing of such gelatinous reaction mixtures. In patent application EP-A-783 005 a process is described for the continuous production of superabsorbent polymers, in which aqueous emulsions of crosslinked or uncrosslinked polyacrylonitrile homopolymers and/or copolymers are hydrolysed in a mixing and kneading, long-retention-time reactor ("List reactor") which operates continuously for the implementation of high-viscosity reactions by reaction with aqueous alkali-hydroxide solutions at 70 to 100° C., and from the highly viscous gels which form in this process the superabsorbent polymer precipitates out continuously in the form of easily filterable powder as a result of continuous precipitation with low-boiling monoalcohols (ethanol, methanol). After drying and grinding to the desired particle-size range, the finished superabsorber is then obtained. Such an apparatus is technically demanding in comparison with conventional reactors. The object, therefore, was to find an alternative, clearly simplified process.

SUMMARY OF THE INVENTION

It has now been found that superabsorbent polymers can be produced from PAN emulsions continuously in conventional reactors if the hydrolysis of PAN emulsions is carried out in an aqueous-alcoholic medium with the removal of ammonia. The alcohol serves as a diluent for the highly viscous intermediate stage which arises in the course of the hydrolysis as well as a precipitating agent. In the course of hydrolysis the fine-particle emulsions based on polyacrylonitrile pass over into an easily stirrable suspension. As a result, it becomes possible to implement the hydrolysis stage continuously in the form of a well stirrable suspension in a cascade of stirred tanks.

DETAILED DESCRIPTION OF THE INVENTION

Figure 1:
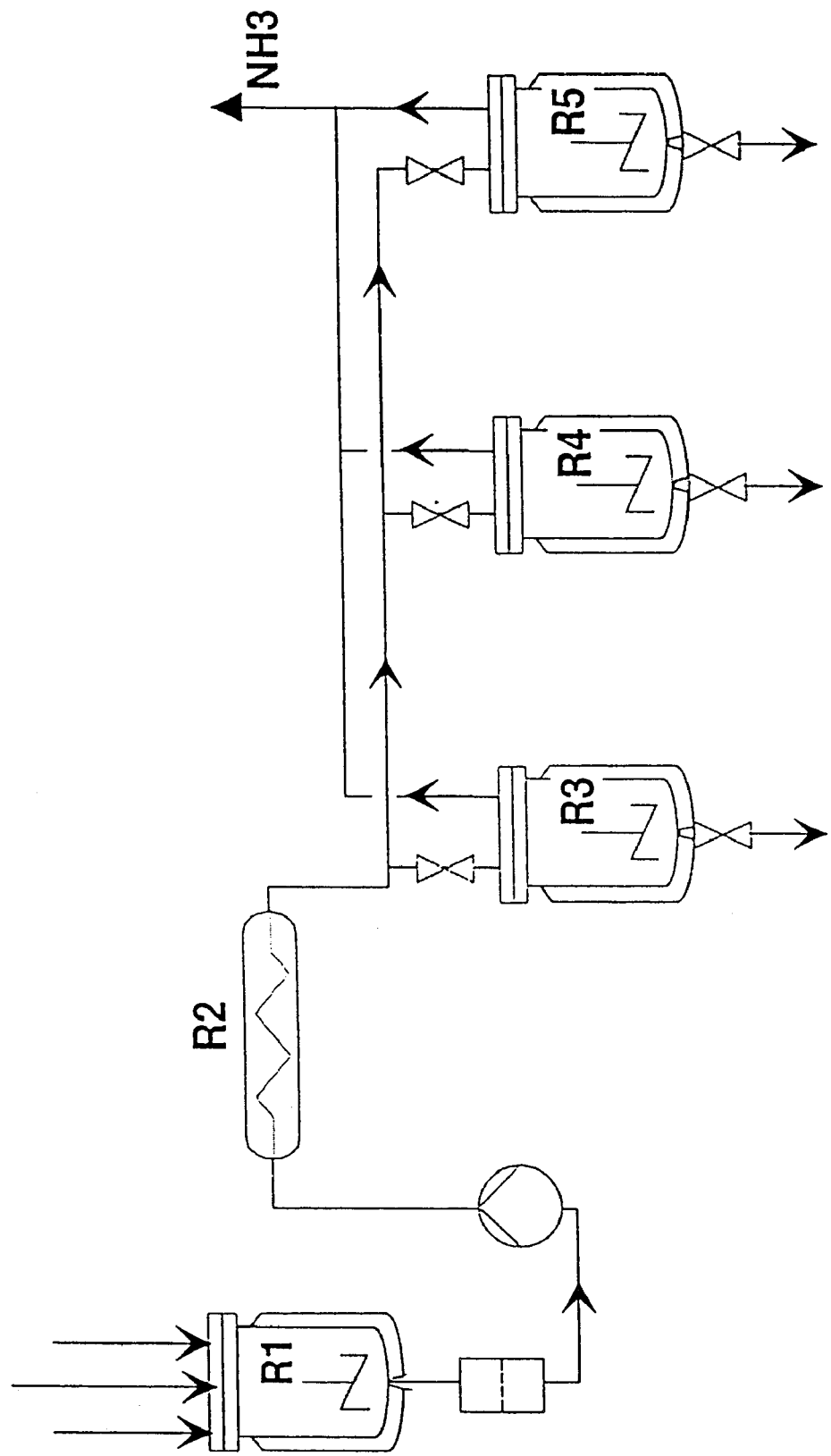
FIG. 1 shows the cascade of five reactors used in carrying out the production described more fully in Example 1.

The invention provides a process for producing superabsorbent polymers, characterised in that crosslinked or uncrosslinked, fine-particle, aqueous polyacrylonitrile emulsions are hydrolysed in a continuously operating cascade of stirred tanks by reaction with alkali-hydroxide solution in an aqueous-alcoholic medium at 60 to 100° C.

The invention further provides a process for producing superabsorbent polymers, in which crosslinked or uncrosslinked, aqueous polyacrylonitrile emulsions are caused to be converted in a continuously operating cascade of stirred tanks by reaction with alkali-hydroxide solution in an aqueous-alcoholic medium at 60 to 100° C., preferably 65 to 80° C., for 0.5 to 3 hours, preferably for 1 to 2 hours. In this process the molar ratio of the nitrile groups of the initial polymers to the hydroxyl groups of the alkali hydroxides lies within the range from 1:0.5 to 1:1.

The cascade of reactors for producing superabsorbent polymers by alkaline hydrolysis of PAN emulsions in a water/alcohol mixture consists of three or more stirred tanks arranged in a series, a premixing of the educts being carried out in the first tank, the prehydrolysis stage being implemented in a subsequent tank, and the actual hydrolysis stage being implemented in a further subsequent tank.

As an alternative, the prehydrolysis stage may also be performed in a tubular reactor.

For implementing the hydrolysis stage, use may be made of two or more reactors (stirred tanks) which are operated in alternating manner. By this means, the subsequent steps of precipitation and neutralisation of the superabsorbent polymer can be carried out without interruption, immediately subsequent to the hydrolysis.

The transport of materials from one reactor to another may be effected by gravity and therefore requires no transport pumps.

Primary, aliphatic monoalcohols, preferably methanol, ethanol, n-propanol, n-butanol, are employed by way of alcohols. The weight ratio of water to alcohol amounts to 1:0.4 to 1:2.

The weight ratio of polyacrylonitrile to water lies within the range from 1:2 to 1:6, preferably 1:2 to 1:5, in particular 1:3 to 1:4.5. It has been found that products having variable degrees of crosslinking and a wide range of predetermined properties may be obtained from uncrosslinked and crosslinked PAN emulsions by changing the weight ratios of water to alcohol and also by selecting the type of alcohol (precipitating power).

The superabsorbent polymers that can be obtained in such a manner exhibit excellent technical application properties. For instance, the products that have been produced from uncrosslinked PAN emulsions attain the following degrees of swelling: 150 g/g to 500 g/g in de-ionized water and 29 to 55 gig in 0.9-% NaCl solution.

If the superabsorbers that have been prepared in the manner described above are subjected in addition to a subsequent surface modification such as is described in patent application EP-A-936 223, for example, the products also display, in addition to their high swelling power, excellent anti-gelblocking properties, which are expressed in high Absorbency Under Load (AUL) values at 0.3 psi and also at 0.7 psi. In addition, these products contain very low water-soluble portions as is more fully described below.

In accordance with the invention the superabsorbent polymers according to the invention are employed and used, for example, in hygiene products such as babies' nappies and incontinence articles, as water-storing materials in agriculture, or in connection with the sheathing of electrical cables. The objects and materials listed are likewise subject-matter of the invention.

EXAMPLES

Example 1

The apparatus that is used for producing superabsorbent polymers by the process according to the invention consists of a cascade of five reactors. Reactor One (R1: stirred tank with a free volume of 10 l) serves for premixing the reactants. Reactor Two (R2: tubular reactor with a free internal volume of about 2.0 l, with a tube diameter of 1.6 cm and total length of 10 m) serves for the heating and prehydrolysis of PAN emulsions. In Reactors Three, Four and Five (R3, R4, R5), which are operated in alternating manner and which are stirred tanks each having a free volume of 10 l, the hydrolysis subject to elimination of ammonia, the post-precipitation and the neutralisation of the superabsorbers take place. Then these reactors are discharged and the aqueous-alcoholic suspensions are supplied to the further processing steps such as filtration, drying, grinding, sieving as well as surface modification.

Continuous transport of the reaction mixture from the second reactor (R2) to reactors R3, R4 and R5 is effected by gravity at a rate of 3 to 6 l/h. A pump is required merely for feeding the low-viscosity reactants from R1 to R2.

For the hydrolysis, an uncrosslinked polyacrylonitrile emulsion was employed having a solids content of 28.0 wt. % and a viscosity index $\eta$ value of 8.6 dl/g as well as an average particle size of 120 nm.

With the aid of pumps, the PAN emulsions are dosed at a flow-rate of 2.968 kg/h; ethanol and a 46-wt. % aqueous solution of NaOH are each dosed at a flow-rate of 2.091 kg/h into the first stirred tank (R1) for premixing. The premixing is carried out at a temperature of 10 to 20° C.

At the start of the hydrolysis the initial reaction mixture exhibits the following composition:

| | |
|---|---|
| Concentration of polyacrylonitrile ([PAN]): | 13.40 wt. % |
| Concentration of sodium hydroxide solution ([NaOH]): | 7.58 wt. % |
| Molar ratio of PAN to NaOH: | 1:0.75 |
| Concentration of ethanol: | 33.20 wt. % |
| Concentration of water: | 45.46 wt. % |
| Weight ratio of water to ethanol: | 1:0.73 |
| Weight ratio of PAN to water: | 1:3.39 |

The % are in relation to the weight of the reaction mixture.

With the aid of a pump the initial reaction mixture is fed at a flow-rate of 6.058 kg/h into the second reactor (R2), where it is preheated to a temperature of 65–70° C. and prehydrolysed. The dwell-time in reactor R2 amounts to about 20 minutes.

The degree of conversion of the nitrile groups after the prehydrolysis amounts to about 35 mol. % (determined by IR spectroscopy).

After this, for further hydrolysis, the reaction mixture flows continuously from the second reactor (R2) to reactors R3, R4, R5, which are operated in alternating manner. If, for example, reactor R3 is filled with the reaction mixture (about 6.0 l), reactors R2 and R4 are interconnected and the transport of material then proceeds from R2 to R4 etc. While reactors R4 and R5 are filling up, the hydrolysed reaction mixture in reactor R3 can be subjected to further processing. By virtue of this manner of proceeding, a continuous operation of the apparatus that has been described is achieved.

In reactor R3 the dwell-time for the reaction mixture amounts to a total of 2 hours at a hydrolysis temperature of 76 to 78° C. The gaseous ammonia arising in the course of the hydrolysis is removed from the reactor during the reaction via special discharge openings and a reflux condenser and subsequent absorption in water or by low-temperature condensation.

After the hydrolysis reaction the reaction mixture is precipitated out, subject to stirring, with additional 2.0 kg ethanol at a temperature of 45 to 50° C. for about 10–15 min. and then the stirrer is switched off. After precipitation of the product, 3.88 kg of the water/alcohol mixture are removed from the reaction mixture by suction from above. Then 2.0 kg of a water/ethanol mixture are again charged into the reactor.

After 10 minutes of stirring this suspension, a pH value between 6 and 7 is adjusted with 390 g of 20-% acetic acid. After neutralisation, the contents of the reactor are let out via the bottom valve.

In reactors R4 and R5 the hydrolysis, precipitation and neutralisation are carried out under the same conditions as in reactor R3.

The superabsorber suspension having a solids content of 21 wt. % which is obtained is then filtered. After filtration and washing with a water/ethanol mixture, the raw product having a solids content of 36.5 wt. % which is obtained is dried at a temperature between 70 and 80° C. in a circulating-air cabinet. Then the product is ground to a particle-size range from 100 to 850 μm.

Determination of the degree of swelling:

250 mg of the superabsorbent polymer to be examined are weighed out into a 300-ml glass beaker and are covered by having 250 ml to 300 ml of distilled water or 50 ml of a 0.9 wt. % NaCl solution poured over and are allowed to stand.

After the equilibrium-swelling state has been attained, the gel which is obtained is filtered off with the aid of a filter cloth having a mesh size of 30 μm or a paper filter and is weighed out. The degree of swelling is then calculated from the ratio of weighed-out sample to weighed-in sample in g/g. Each determination is carried out three times. The accuracy of measurement amounts to ±5%.

For the product that was prepared in accordance with Example 1, a degree of swelling results amounting to 300 g/g in distilled water and 47 g/g in 0.9-% NaCl solution.

Determination of the pH value:

The pH value of the product obtained in accordance with Example 1 amounts to 6.5 in 0.9-% NaCl solution.

Determination of the water-soluble portion (WSP):

0.5 g of the superabsorbent polymer is swollen up in 500 ml of de-ionized water and stirred for 16 hours at 20° C. After filtration of the gel, the WSP is obtained from the determination of the solids content in the filtrate and in the wash water. Said WSP value amounts to 5.9 wt. % in the case of the product obtained in accordance with Example 1.

Examples 2 to 6

The conditions of hydrolysis of the samples produced in accordance with Examples 2 to 6 are summarised in Table 1. For these examples the hydrolysis of the PAN emulsion was carried out in a water/ethanol mixture in a manner corresponding to the method specified in Example 1. In these examples the conditions of hydrolysis (the concentration of PAN in the reaction mixture, the molar ratio of PAN to NaOH, the weight ratio of PAN to water, the dwell-time) were varied.

In the last four columns of Table 1 the degrees of swelling of the products in distilled water and in 0.9-% NaCl solution, as well as the pH values and the water-soluble portions of the products with particle sizes from 100 to 850 μm are recorded. From the results that are summarised in Table 1 it is clearly evident that, by virtue of the process according to the invention, products having superabsorbent properties are obtained from uncrosslinked PAN emulsions and variable but controllable technical properties are obtained by changing the water/alcohol and PAN/water ratios. It can accordingly be established that "tailor made products" can be produced by the process according to the invention.

For further improving the technical properties, the superabsorbent polymers that were produced in accordance with Examples 1 to 6 were subsequently subjected to a surface modification with formaldehyde and silicic acid, as described in European Patent Application EP-A 936 223.

The technical properties of the modified superabsorbers that were obtained in accordance with Examples 1 to 6 are compiled in the following Table 2. In this connection the following properties were measured:

absorption substantially according to the cylinder method as described in U.S. Pat. No. 5,408,019 incorporated by reference herein. In Table 2, the values obtained after 30 minutes are listed.

retention (according to "edana" specification 440.0-96)

AUL (Absorbency Under Load) at 0.3 psi and 0.7 psi (according to "edana" specification 440.0-96)

In addition, in Table 2 the water-soluble portions (WSP), the pH values and the results of Rewet measurements in respect of the superabsorbent polymers produced in accordance with Examples 2, 4 and 6 are specified. All the investigations were carried out with 0.9-% NaCl solution.

Rewet measurements serve to demonstrate that the superabsorbent polymers are able to retain body fluids, also under pressure, under practical conditions such as in baby diapers, for example. In these measurements, 5 g of superabsorber are uniformly distributed in a cellulose fluff having an area of 13×21 cm and are then covered by having 70 ml of a 0.9-% NaCl solution poured over. The surface is then covered with a stack of filter paper and a load of 4 kg is applied for 15 sec. After measurement of the increase in weight of the filter papers, this operation—charging of 70 ml of fluid and renewed loading with 4 kg—is repeated a further two times.

The increase in weight of the filter papers that is measured after each testing procedure constitutes a measure of the capacity of the superabsorbers to retain liquid even subject to considerable loading.

TABLE 1

| | Conditions of hydrolysis | | | | | | | | Content of | Degree | | | |
| | Composition of initial reaction mixture | | | | | | | | Carbox- | of swelling | | pH value | |
| Example No. | [PAN] wt. % | [NaOH] wt. % | MR* PAN: NaOH | [ethanol] wt. % | [water] wt. % | W.R.** water: ethanol | WR PAN: water | T, ° C. | DT*** min. | ylate groups mol. % | in water | in 0.9-% NaCl solution | in 0.9-% NaCl solution | WSP, wt. % |
|---|---|---|---|---|---|---|---|---|---|---|---|---|---|---|
| 1. | 13.4 | 7.58 | 1:0.75 | 33.2 | 45.46 | 1:0.73 | 1:3.39 | 76–78 | 120 | 67 | 310 | 47.0 | 6.5 | 5.9 |
| 2. | 13.73 | 7.45 | 1:0.72 | 33.8 | 44.62 | 1:0.76 | 1:3.25 | 76–78 | 150 | 65 | 300 | 45.0 | 6.5 | 6.0 |
| 3. | 12.86 | 7.76 | 1:0.8 | 35.41 | 43.6 | 1:0.812 | 1:3.39 | 76–78 | 160 | 72 | 330 | 49.0 | 6.5 | 5.8 |
| 4. | 14.2 | 7.45 | 1:0.7 | 34.1 | 43.88 | 1:0.78 | 1:3.09 | 76–78 | 160 | 64 | 270 | 44.0 | 6.1 | 4.5 |
| 5. | 14.0 | 7.92 | 1:0.75 | 43.6 | 34.1 | 1:1.28 | 1:2.35 | 76–78 | 160 | 70 | 160 | 29.5 | 6.5 | 2.25 |
| 6. | 12.3 | 7.58 | 1:0.75 | 28.1 | 51.66 | 1:0.54 | 1:4.2 | 76–78 | 120 | 69 | 390 | 51 | 6.4 | 7.1 |

*MR - Molar Ratio
**WR - Weight Ratio
***DT - Dwell-Time
WSP - Water-Soluble Portion

TABLE 2

| Example No. | Absorption (cylinder) [g/g] | Retention [g/g] | AUL [g/g] | | WSP [wt. %] | pH value | Rewet [g] | | |
|---|---|---|---|---|---|---|---|---|---|
| | | | 0.3 PSI | 0.7 PSI | | | 1st measurement | 2nd measurement | 3rd measurement |
| 1 | 46.3 | 26.2 | 26.0 | 16.7 | 5.8 | 6.4 | — | — | — |
| 2 | 48.8 | 26.0 | 26.8 | 15.0 | 6.0 | 6.4 | 0.03 | 0.14 | 0.79 |
| 3 | 45.7 | 25.7 | 25.4 | 19.5 | 5.8 | 6.5 | — | — | — |
| 4 | 46.5 | 25.6 | 27.9 | 16.8 | 4.3 | 6.1 | 0.03 | 0.06 | 0.32 |
| 5 | — | — | — | — | — | — | — | — | — |
| 6 | 46.3 | 28.7 | 25.9 | 19.4 | 6.9 | 6.32 | 0.02 | 0.09 | 0.39 |

What is claimed is:

1. A process for producing a superabsorbent polymer comprising continuously hydrolysing an aqueous emulsion of crosslinked or uncrosslinked polyacrylonitrile in the form of fine particles in a cascade of stirred tanks by reacting the educt of polyacrylonitrile with alkali-hydroxide solution in an aqueous-alcoholic medium at 60 to 100° C.

2. The process of claim 1 wherein the duration of the hydrolysing is 0.5 to 3 hours.

3. The process of claim 1 wherein the molar ratio of the nitrile groups of the polyacrylonitrile to the hydroxyl groups of the alkali hydroxide is between 1:0.5 and 1:1.

4. The process of claim 1 wherein the educt is premixed in a first tank of said cascade, prehydrolysis stage is implemented in a second tank of said cascade, and a hydrolysis stage is implemented in a third tank of said cascade.

5. The process of claim 4, wherein the second tank is a tubular reactor.

6. The process of claim 1 wherein the aqueous alcoholic medium contains at least one primary, aliphatic monoalcohol.

7. The process of claim 6 wherein said monoalcohol is selected from the group consisting of methanol, ethanol, n-propanol, and n-butanol.

8. The process of claim 1 wherein weight ratio of water to alcohol in said aqueous alcoholic medium is 1:0.4 to 1:2.

9. The process of claim 1 wherein polyacrylonitrile and water are present in the aqueous emulsion at a weight ratio of polyacrylonitrile to water of 1:2 to 1:6.

10. The superabsorbent polymer produced by the process of claim 1.

11. A process for producing a superabsorbent polymer comprising continuously hydrolysing an aqueous emulsion of crosslinked or uncrosslinked polyacrylonitrile in the form of fine particles in a cascade of stirred tanks by reacting the polyacrylonitrile with alkali-hydroxide solution in an aqueous-alcoholic medium at 60 to 100° C. and removing the resulting gaseous ammonia.

* * * * *